United States Patent
Evans et al.

(10) Patent No.: US 11,491,141 B1
(45) Date of Patent: Nov. 8, 2022

(54) METHODS OF TREATING GLUTATHIONE DEFICIENCIES AND DEFICIENCIES IN GLUTATHIONE SYNTHETASE ACTIVITY

(71) Applicant: Nanjing Nutrabuilding Bio-tech Co., Ltd., Nanjing (CN)

(72) Inventors: Joseph L. Evans, St. Louis, MO (US); Qiru Fan, Nanjing (CN); Shawn Wells, Lewisville, TX (US); Kylin Liao, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 0 days.

(21) Appl. No.: 17/569,563

(22) Filed: Jan. 6, 2022

(51) Int. Cl.
*A61K 31/4164* (2006.01)
*A61K 31/4172* (2006.01)
*A61P 25/00* (2006.01)
*C07D 233/84* (2006.01)

(52) U.S. Cl.
CPC .............................. *A61K 31/4172* (2013.01)

(58) Field of Classification Search
CPC . A61K 31/4164; A61K 31/4172; A61P 25/00; C07D 233/84
See application file for complete search history.

(56) References Cited

U.S. PATENT DOCUMENTS 8,399,500 B2    3/2013   Erdelmeier

FOREIGN PATENT DOCUMENTS

WO    2021/102736 A1    6/2021

OTHER PUBLICATIONS

Beelman, et al.; Perspectives in Nutritional Science, Is ergothioneine a 'longevity vitamin' limited in the American diet?; Journal of Nutritional Science (2020), vol. 9, e52, 5 pp.
Borodina, et al.; The biology of ergothioneine, an antioxidant nutraceutical, Nutrition Research Reviews (2020), 33, 190-217.
Deiana, et al.; L-Ergothioneine modulates oxidative damage in the kidney and liver of rats in vivo: studies upon the profile of polyunsaturated fatty acids, Elsevier, Clinical Nutrition (2004) 23, 183-193.
Halliwell, Barry; The antioxidant paradox: less paradoxical now?; British Journal of Clinical Pharmacology; published Mar. 15, 2012, 8pp.
Harvey, et al.; Nrf2-regulated glutathione recycling independent of biosynthesis is critical for cell survival during oxidative stress; NIH Public Access; Author Manuscript; Free Radic Biol Med. Feb. 15, 2009; 46(4): 443-453. doi:10.1016/j.freeradbiomed.2008.10.040.
Minisch, et al.; A Review of Dietary (Phyto)Nutrients for Glutathione Support; Nutrients 2019, 11, 2073; doi:10.3390/nu11092073; 20 pp.
Pizzorno, J.; The path Ahead-Glutathione!; Integrative Medicine, vol. 13, No. 1; Feb. 2014; 5 pp.
Song, et al.; Ergothioneine protects against neuronal injury induced by cisplatin both in vitro and in vivo; Elsevier; Food and Chemical Toxicology 48 (2010) 3492-3499.
Song, et al.; Ergothioneine and melatonin attenuate oxidative stress and protect against learning and memory deficits in C57BL/6J mice treated with D-galactose; Informa Healthcare; Free Radical Research; 33 pp.
Zalachoras, et al.; Therapeutic potential of glutathione-enhancers in stress-related psychopathologies; Elsevier; Neuroscience and Biobehavioral Reviews 114 (2020) 134-155.

*Primary Examiner* — Brenda L Coleman
(74) *Attorney, Agent, or Firm* — Clark G. Sullivan

(57) ABSTRACT

Glutathione deficiencies and deficiencies in glutathione synthetase activity, and therapeutic methods for the treatment thereof.

18 Claims, 1 Drawing Sheet

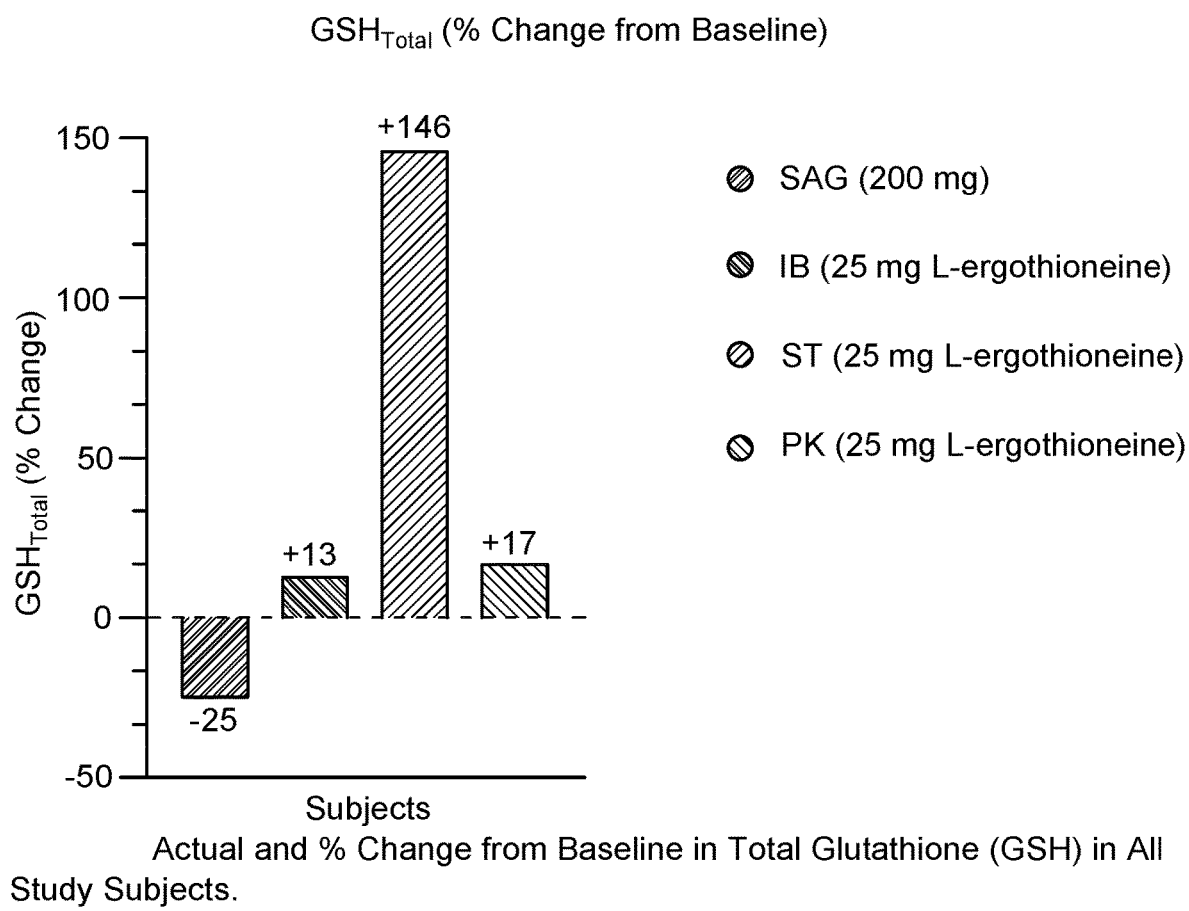
Actual and % Change from Baseline in Total Glutathione (GSH) in All Study Subjects.

METHODS OF TREATING GLUTATHIONE DEFICIENCIES AND DEFICIENCIES IN GLUTATHIONE SYNTHETASE ACTIVITY

FIELD OF THE INVENTION

The present invention relates to glutathione deficiencies and deficiencies in glutathione synthetase activity, and to therapeutic methods for the treatment thereof.

BACKGROUND OF THE INVENTION

Glutathione synthetase deficiency (OMIM 231900 and OMIM 266130) is a rare disorder characterized by a deficiency of the enzyme glutathione synthetase. This enzyme is part of the chemical process by which the body creates glutathione, a protein molecule that plays a role in many cell processes. Glutathione synthetase deficiency is often classified as mild, moderate or severe. Consequently, the specific symptoms and severity can vary greatly from one person to another. Generally, the mild form (OMIM 231900) only affects red blood cells (erythrocytes). The severe form (OMIM 266130) is widespread (generalized) affecting many types of cells of the body. The moderate form falls in between these two extremes. All forms of this rare disorder are caused by alterations (mutations) in the GSS gene and are inherited in an autosomal recessive manner.

Glutathione is a tripeptide (cysteine, glycine, and glutamic acid) found in relatively high concentrations in many bodily tissues. It plays a pivotal role in reducing oxidative stress, maintaining redox balance, enhancing metabolic detoxification, and regulating the immune system. Various chronic, age-related diseases such as those related to neurodegeneration, mitochondrial dysfunction, and even cancer, have been related to suboptimal or deficient glutathione levels. There is increasing awareness of its utility in mitigating body toxin load through its ability to enhance hepatic conversion and excretion of compounds such as mercury and persistent organic pollutants (POPs). Pizzorno J. Glutathione! Integr. Med. 2014; 13:8-12.

As a result, it is possible that supporting the body's endogenous levels of glutathione would be important for maintaining health and mitigating disease, although clear causal relationships between low glutathione and disease risk remain to be determined. One confounding factor is the complexity of antioxidants, referred to by Halliwell as the "antioxidant paradox", or the situation in which antioxidants such as glutathione can possess prooxidant activity causing a hormetic effect enabling the body to bolster its endogenous antioxidant defenses. Indeed, redox balance can be the cause or consequence of a disease, and in some cases, it is difficult to know the level at which an antioxidant becomes a prooxidant. Therefore, there is much to understand about the role of glutathione levels in health. Halliwell B. The antioxidant paradox: less paradoxical now? Br. J. Clin. Pharmacol. 2013; 75:637-644.

One factor influencing glutathione status, as discussed above in connection with glutathione synthetase deficiency (OMIM 231900 and OMIM 266130), is the degree of variability in an individual's capacity to produce glutathione, mainly due to genetic variability in enzymes involved in its production and/or regeneration. In addition, human clinical research suggests that nutritional interventions, including amino acids, vitamins, minerals, phytochemicals, and foods can have important effects on glutathione synthetase activity and/or circulating glutathione which may translate to clinical benefit.

It would seem to be most efficient to administer oral glutathione directly to override the effects of potentially inefficient enzymes. However, some studies have shown no change in glutathione levels or in parameters of oxidative stress despite acute or chronic (four weeks) oral glutathione supplementation, potentially due to peptidase degradation during the digestive process. There is also some evidence to the contrary. One six-month, randomized, double-blinded, placebo-controlled trial found that taking oral glutathione at either 250 or 1000 mg/day led to significant increases in the body stores of glutathione in 54 non-smoking adults in a dose-dependent manner. There was also a decrease in the markers for oxidative stress at six months as indicated through an improvement in the oxidized (GSSG) to reduced (GSH) glutathione ratio in whole blood, in conjunction with favorable increases in natural killer cell cytotoxicity. Deanna M. Minich, and Benjamin I. Brown. A Review of Dietary (Phyto)Nutrients for Glutathione Support. Nutrients 2019, 11, 2073.

Several lines of evidence also indicate that Nrf2 plays a key role in the regulation of cellular GSH homeostasis: (i) there is low GSH or a loss of induction of GSH in Nrf2-/- cells and tissues; (ii) Nrf2 regulates GSH biosynthesizing enzymes (GCLM, GCLC); (iii) Nrf2 regulates the cysteine/glutamate exchange transporter that maintains intracellular GSH levels by regulating cysteine influx; and (iv) Nrf2 regulates GPX2 and GST, which use GSH as a cofactor. In addition, several researchers have shown that in response to oxidative stress, Nrf2-/- cells and tissues accumulate greater levels of GSSG than wild-type Nrf-2 cells. C. J. Harvey, R. K. Thimmulappa, A. Singh, D. J. Blake, G. Ling, N. Wakabayashi, J. Fujii, A. Myers, and S. Biswal. Nrf2-regulated glutathione recycling independent of biosynthesis is critical for cell survival during oxidative stress. Free Radic Biol Med. 2009 Feb. 15; 46(4): 443-453.

L-ergothioneine is a thiolhistidine derivative, first isolated from rye ergot (*Claviceps purpurea*) in 1909. It occurs naturally in common foods, including mushrooms, offal, cereals, and some varieties of black and red beans (*Phaseolus vulgaris*). It is chemically defined as (2S)-3-(2-thioxo-2,3-dihydro-1H-imidazol-4-yl)-2-(trimethylammonio)-propanoate, and has the following chemical structure:

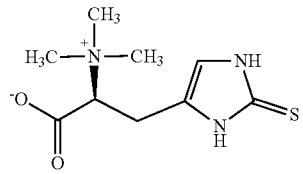

"Safety of synthetic 1-ergothioneine (Ergoneine®) as a novel food pursuant to Regulation (EC) No 258/97", *EFSA Journal* (2016) 14(11).

Various sources of L-ergothioneine are marketed commercially, including a mushroom extract marketed by Blue California (Tomas, RSM, CA) and a chemically synthesized compound manufactured by Tetrahedron, Vincennes, France (U.S. Pat. No. 8,399,500 B2). A production process using a genetically modified *S. cerevisiae* was recently proposed by van der Hoek S A et al. (2019) "Engineering the yeast *Saccharomyces cerevisiae* for the production of L-(þ)-ergothioneine." Front Bioeng Biotechnol 7, 262.

The European Food Safety Authority ("EFSA") previously reviewed a petition for the use of synthetic L-ergothioneine as a novel food ingredient at levels of up to 5 mg per serving in specific conventional foods, including alcohol-free beverages, cereal bars, milk, fresh dairy products, and chocolates, and in dietary supplements with a recommended maximum daily dose of 30 mg L-ergothioneine per day for adults and 20 mg L-ergothioneine per day for children. EFSA (2016). L-ergothioneine has been reported to be a "longevity" vitamin because of its anti-inflammatory activities and its ability to reduce oxidative stress. Beelman et al., "Is ergothioneine a 'longevity vitamin' limited in the American diet?" Journal of Nutritional Science (2020), vol. 9, e52.

What is needed are methods of improving glutathione status and glutathione synthetase activity, particularly in patients suffering from a deficiency of glutathione of glutathione synthetase activity.

SUMMARY OF INVENTION

It has unexpectedly been discovered that L-ergothioneine increases glutathione concentrations and glutathione synthetase activity, making the compound particularly useful for the treatment of conditions associated with deficiencies in glutathione and glutathione synthetase activity. These effects have been observed from a novel form of L-ergothioneine produced from *S. cerevisiae*, not affected by the D-isomer of ergothioneine or the amino acid impurities (particularly any thiohistidine derivatives other than L-ergothioneine such as S-methyl-ergothioneine or selenium-containing selenoneine) that affect currently available sources of L-ergothioneine. Thus, in a first principal embodiment the invention provides a method a method of treating a glutathione deficiency in a human patient in need thereof comprising administering to the patient a therapeutically effective amount of L-ergothioneine or a pharmaceutically acceptable salt thereof.

In a second principal embodiment the invention provides a method of treating a glutathione synthetase deficiency optionally causing hemolytic anemia in a human patient in need thereof comprising administering to the patient a therapeutically effective amount of L-ergothioneine or a pharmaceutically acceptable salt thereof. In one particular embodiment the patient has glutathione synthetase deficiency causing hemolytic anemia (OMIM 231900).

In a third principal embodiment the invention provides a method of treating a generalized glutathione synthetase deficiency optionally with 5-oxoprolinuria in a human patient in need thereof comprising administering to the patient a therapeutically effective amount of L-ergothioneine or a pharmaceutically acceptable salt thereof. In one particular embodiment the patient is suffering from glutathione synthetase deficiency with 5-oxoprolinuria (OMIM 266130).

The inventors have also unexpectedly discovered an improvement in Nrf2 regulated genetic activity from the administration of L-ergothioneine, having particularly utility in the treatment of conditions associated with deficiencies in glutathione and glutathione synthetase activity. Thus, in a fourth principal embodiment the invention provides a method of treating a glutathione deficiency characterized by a reduction in Nrf2 regulated genetic activity in a human patient in need thereof comprising administering to the patient a therapeutically effective amount of L-ergothioneine or a pharmaceutically acceptable salt thereof.

In a fifth principal embodiment the invention provides a method of treating a glutathione synthetase deficiency characterized by a reduction in Nrf2 regulated genetic activity optionally causing hemolytic anemia in a human patient in need thereof comprising administering to the patient a therapeutically effective amount of L-ergothioneine or a pharmaceutically acceptable salt thereof. In one particular embodiment the patient has glutathione synthetase deficiency causing hemolytic anemia (OMIM 231900).

In a sixth principal embodiment the invention provides a method of treating a generalized glutathione synthetase deficiency characterized by a reduction in Nrf2 regulated genetic activity optionally with 5-oxoprolinuria in a human patient in need thereof comprising administering to the patient a therapeutically effective amount of L-ergothioneine or a pharmaceutically acceptable salt thereof in one particular embodiment the patient is suffering from glutathione synthetase deficiency with 5-oxoprolinuria (OMIM 266130).

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURE

The accompanying drawings, which are incorporated in and constitute a part of this specification, illustrate several embodiments of the invention and together with the description serve to explain the principles of the invention.

The FIGURE depicts the percent change in baseline in total glutathione in the patients treated in Example 2.

DETAILED DESCRIPTION

Definitions and Use of Terms

As used in the specification and claims, the singular forms a, an, and the include plural references unless the context clearly dictates otherwise. For example, the term "a specification" refers to one or more specifications for use in the presently disclosed methods and systems. "An ingredient" includes mixtures of two or more such ingredients, and the like. The word "or" or like terms as used herein means any one member of a particular list and also includes any combination of members of that list.

When used herein the term "about" will compensate for variability allowed for in the pharmaceutical industry and inherent in products in this industry, such as differences in product strength due to manufacturing variation and time-induced product degradation, as well as differences due to waters of hydration and different salts. The term also allows for any variation which in the practice of good manufacturing practices would allow the product being evaluated to be considered therapeutically equivalent or bioequivalent in humans to the recited strength of a claimed product. In some embodiments the term allows for any variation within 5% or 10% of the recited specification or standard.

As used in this specification and in the claims which follow, the word "comprise" and variations of the word, such as "comprising" and "comprises," means "including but not limited to," and is not intended to exclude, for example, other additives, components, integers or steps. When an element is described as comprising one or a plurality of components, steps or conditions, it will be understood that the element can also be described as "consisting of" or "consisting essentially of" the component, step or condition, or the plurality of components, steps or conditions.

"Therapeutically effective amount" means that amount which, when administered to a human for supporting or affecting a metabolic process, or for treating or preventing a disease, is sufficient to cause such treatment or prevention of the disease or supporting or affecting the metabolic process. In any of the embodiments or subembodiments of this invention, a therapeutically effective amount is capable of increasing glutathione concentrations in a patient deficient in glutathione or glutathione synthetase activity.

When ranges are expressed herein by specifying alternative upper and lower limits of the range, it will be understood that the endpoints can be combined in any manner that is mathematically feasible. Thus, for example, a range of from 50 or 80 to 100 or 70 can alternatively be expressed as a series of ranges of from 50 to 100, from 50 to 70, and from 80 to 100. When a series of upper bounds and lower bounds are related using the phase "and" or "or", it will be understood that the upper bounds can be unlimited by the lower bounds or combined with the lower bounds, and vice versa. Thus, for example, a range of greater than 40% and/or less than 80% includes ranges of greater than 40%, less than 80%, and greater than 40% but less than 80%. Unless otherwise specified by the term "between," the boundaries of the range (lower and upper ends of the range) are included in the claimed range and can be preceded by the term "about."

When an element of a process or thing is defined by reference to one or more examples, components, properties or characteristics, it will be understood that any one or any combination of those components, properties or characteristics can also be used to define the matter at issue. This might occur, for example, when specific examples of an element are recited in a claim (as in a Markush grouping), or an element is defined by a plurality of characteristics. Thus, for example, if a claimed system comprises element A defined by elements A1, A2 and A3, in combination with element B defined by elements B1, B2 and B3, the invention will also be understood to cover a system defined by element A without element B, a system in which element A is defined by elements A1 and A2 in combination with element B defined by elements B2 and B3, and all other possible permutations.

"OMIM" refers to the Online Mendelian Inheritance in Man®, An Online Catalog of Human Genes and Genetic Disorders, as Updated on Dec. 30, 2021 (the "OMIM Catalog"). An OMIM number refers to the genetic disorder associated with the number as published in the Catalog on Dec. 30, 2021.

Glutathione synthetase deficiency refers to a condition in which glutathione synthetase activity is impaired, slowed, or lessened, whether by a deficiency in the synthetase enzymes, a defect in synthetase enzyme sequences, a deficiency in synthetase substrates or supporting nutritional co-factors, or any other cause of such impaired activity. A glutathione synthetase deficiency by definition will lead to a glutathione deficiency in the absence of exogenous glutathione supplementation. Conversely, a glutathione deficiency necessarily implies a glutathione synthetase deficiency. Thus, when the term "deficiency" is used herein, it will refer to glutathione deficiency or glutathione synthetase deficiency or both.

Discussion of Principal Embodiments

A first principal embodiment of the invention provides a method a method of treating a glutathione deficiency in a human patient in need thereof comprising administering to the patient a therapeutically effective amount of L-ergothioneine or a pharmaceutically acceptable salt thereof.

A second principal embodiment of the invention provides a method of treating a glutathione synthetase deficiency optionally causing hemolytic anemia in a human patient in need thereof comprising administering to the patient a therapeutically effective amount of L-ergothioneine or a pharmaceutically acceptable salt thereof. In one particular embodiment the patient has glutathione synthetase deficiency causing hemolytic anemia (OMIM 231900).

A third principal embodiment of the invention provides a method of treating a generalized glutathione synthetase deficiency optionally with 5-oxoprolinuria in a human patient in need thereof comprising administering to the patient a therapeutically effective amount of L-ergothioneine or a pharmaceutically acceptable salt thereof. In one particular embodiment the patient is suffering from glutathione synthetase deficiency with 5-oxoprolinuria (OMIM 266130).

A fourth principal embodiment of the invention provides a method of treating a glutathione deficiency characterized by a reduction in Nrf2 regulated genetic activity in a human patient in need thereof comprising administering to the patient a therapeutically effective amount of L-ergothioneine or a pharmaceutically acceptable salt thereof.

A fifth principal embodiment of the invention provides a method of treating a glutathione synthetase deficiency characterized by a reduction in Nrf2 regulated genetic activity optionally causing hemolytic anemia in a human patient in need thereof comprising administering to the patient a therapeutically effective amount of L-ergothioneine or a pharmaceutically acceptable salt thereof. In one particular embodiment the patient has glutathione synthetase deficiency causing hemolytic anemia (OMIM 231900).

A sixth principal embodiment of the invention provides a method of treating a generalized glutathione synthetase deficiency characterized by a reduction in Nrf2 regulated genetic activity optionally with 5-oxoprolinuria in a human patient in need thereof comprising administering to the patient a therapeutically effective amount of L-ergothioneine or a pharmaceutically acceptable salt thereof in one particular embodiment the patient is suffering from glutathione synthetase deficiency with 5-oxoprolinuria (OMIM 266130).

Discussion of Subembodiments

The invention can further be understood with reference to various subembodiments which can modify any of the principal embodiments. It will be understood that these subembodiments can be combined in any manner that is both mathematically and physically possible to create additional subembodiments, which in turn can modify any of the principal embodiments. Generally speaking, in any of the embodiments or subembodiments of the present invention, the patient scan be characterized as suffering from a general loss of appetite, early satiety, altered food preferences, or a combination thereof.

In any of the embodiments of the current invention, the patient can be suffering from one or a combination of plasma levels of:

a) plasma reduced glutathione (GSH)≤3.8, 3.5, or 3.2 µmol/L;

b) plasma oxidized glutathione (GSS)≤0.160, 0.130, or 0.100 µmol/L;

c) plasma total glutathione (GSH+GSS)≤3.8, 3.5, or 3.2 µmol/L;

d) GSH RBC levels ≤1,200 or 1,000 or 800 or 600 or 400 or 250 µmol/L; and/or e) GSH RBC levels ≤46.9 or 40 or 35 or 30 or 25 or 20 or 15 mg/dL.

Alternatively or in addition, the patient can be characterized by one or more clinical features associated with glutathione deficiencies. Thus, in any of the embodiments of the current invention the patient can be suffering from one or a combination of:

a) lack of energy;
b) joint and muscle aches and pains;
c) foggy brain;
d) low immunity; and/or
e) poor sleep.

In still further embodiments the patient can be suffering from one or a combination of:

a) anemia;
b) metabolic acidosis;
c) frequent infections;
d) seizures, Alzheimer's disease, or Parkinson's disease;
e) ataxia;
f) liver disease; and/or
g) heart attack or stroke.

The L-ergothioneine also can be characterized by its purity or source of production. In any of the embodiments of the present invention, the L-ergothioneine preferably comprises 0% D-ergothioneine, 0% nucleic acids (particularly any thiohistidine derivatives other than L-ergothioneine such as S-methyl-ergothioneine or selenium-containing selenoneine), 0% amino acids, and less than 2% total impurities. The L-ergothioneine can also be characterized by other aspects of its purity, and in various embodiments comprises less than 0.5%, 0.1%, 0.05%, or 0.01%, of the disulfide of L-ergothioneine.

Depending on the purity profile intended, various methods of manufacturing are disclosed in the prior art that can be used to manufacture the L-ergothioneine used in the current invention, including a chemical synthesis process described by Tetrahedron, Vincennes, France in U.S. Pat. No. 8,399,500 B2, a genetically modified *S. cerevisiae* process described by van der Hoek S A et al. (2019) "Engineering the yeast *Saccharomyces cerevisiae* for the production of L-(þ)-ergothioneine." Front Bioeng Biotechnol 7, 262, and an *E. coli* process described by Nanjing Nutrabuilding Bio-tech Co., Ltd. in WO 2021/102736 A1.

The methods are generally practiced using doses of L-ergothioneine sufficient to increase the concentrations of glutathione or increase glutathione synthetase activity. The dose of L-ergothioneine can vary across a range of suitable doses depending on the health of the subject, the desired response, the dosage form and the route of administration. In a preferred subembodiment when administration is oral, the therapeutically effective amount is from about 15 to about 50 mg/day of L-ergothioneine, from about 15 to about 35 mg/day, preferably from about 20 to about 30 mg/day, and most preferably about 20 or about 25 mg/day. The dose is preferably administered as a single administration once per day, thus comprising 15-50 mg of L-ergothioneine, 15-35 mg of L-ergothioneine, 20-30 mg of L-ergothioneine, or 20 or 25 mg of L-ergothioneine. The most preferred form of the compound is free acid, and the foregoing doses are preferably based on the weight of the free acid.

Dosage Forms/Routes of Administration

Pharmaceutical compositions for preventing and/or treating a subject are further provided comprising a therapeutically effective amount of L-ergothioneine or a pharmaceutically acceptable salt or adduct thereof and one or more pharmaceutically acceptable excipients. A "pharmaceutically acceptable" excipient is one that is not biologically or otherwise undesirable, i.e., the material can be administered to a subject without causing any undesirable biological effects or interacting in a deleterious manner with any of the other components of the pharmaceutical composition in which it is contained. The carrier can be selected to minimize any degradation of the active ingredient and to minimize any adverse side effects in the subject, as would be well known to one of skill in the art. The carrier can be a solid, a liquid, or both.

The disclosed compounds can be administered by any suitable route, preferably in the form of a unit dosage form adapted to such route, and in a dose effective for the treatment or prevention intended. For oral administration, the L-ergothioneine and other ingredients can be enclosed in a hard or soft-shell gelatin capsule, compressed into tablets, or incorporated directly into the individual's diet. Suitable dosage forms include ingestible tablets, buccal tablets, films, powder sachets, troches, capsules, elixirs, suspensions, syrups, wafers, and the like. Such compositions and preparations should contain at least 1% by weight of active compound. The percentage of the compositions and preparations can, of course, be varied and can conveniently be from about 5% to about 80% of the weight of the unit.

Tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor.

EXAMPLES

In the following examples, efforts have been made to ensure accuracy with respect to numbers (e.g., amounts, temperature, etc.) but some errors and deviations should be accounted for. The following examples are put forth to provide those of ordinary skill in the art with a complete disclosure and description of how the methods claimed herein are made and evaluated and are intended to be purely exemplary of the invention and are not intended to limit the scope of what the inventors regard as their invention.

Example 1. Evaluation of the Antioxidant Effects of Compound L-ergothioneine in Normal Human Epidermal Keratinocytes Under Basal or UV-Irradiated Conditions In the present study, the effects of compound L-Ergothioneine were investigated in normal human epidermal keratinocytes (NHEK) under basal or UV-irradiated conditions. More specifically, the effects of this compound were evaluated using RT-qPCR technology. Extracted mRNA was analyzed using a PCR array ("mQPA-8-Nrf2") for the analysis of 8 target genes (including 1 housekeeping gene) selected for their role in Nrf2 pathway. Prior to this assay, a preliminary cytotoxicity assay was performed on compound L-Ergothioneine and Resveratrol (reference in basal condition) using a standard WST-8 reduction assay, in order to determine the concentrations to be tested in this study.

Abbreviations
cDNA Complementary desoxyribonucleic acid
DMSO Dimethyl sulfoxide
DNA Desoxyribonucleic acid
mQPA Marker qPCR array
mRNA Messenger ribonucleic acid
MW Molecular weight
NHEK Normal human epidermal keratinocytes
OD Optical density
PBS Phosphate buffered saline
RE Relative expression
RIN RNA Integrity number
RNA Ribonucleic acid
RT Room temperature
RT-qPCR Reverse transcription quantitative Polymerase chain reaction
Sd Standard deviation
sem Standard error of the mean
SFM Serum free medium
UV Ultraviolet
WST-8 2-(2-methoxy-4-nitrophenyl)-3-(4-nitrophenyl)-5-(2,4-disulfophenyl)-2H-tetrazolium, monosodium salt
Materials and Methods
Biological Model
Cell type: Normal human epidermal keratinocytes (NHEK) used at the 3rd passage
Culture conditions: 37° C., 5% CO2
Culture medium: Keratinocyte-SFM optimized for the assay, supplemented with Epidermal
Growth Factor Pituitary extract
Assay medium: Keratinocyte-SFM optimized for the assay
Test compound: L-Ergothioneine in ultrapure water
Test concentrations: 0.5, 3 and 30 µM
Reference: Resveratrol
Test concentration: 20 µM
Preliminary Cytotoxicity Assay
Cell type: NHEK in assay medium
Incubation time: 24 hours After treatment, the cells were incubated with WST-8 (highly water-soluble tetrazolium salt) reduced in a water-soluble orange colored product (formazan) by succinate dehydrogenase (mitochondrial enzyme). This transformation is proportional to the number of living cells and their metabolic activity. The optical density (OD) of the extracts at 450 nm was recorded with a spectrometer (VERSAmax, Molecular Devices).

Keratinocytes were seeded in 24-well plates and cultured for 24 hours in culture medium and in assay medium for a further 24 hours. The medium was then replaced by assay medium containing or not (control) the compound or Resveratrol and cells were pre-incubated for 24 hours.

After pre-incubation, the medium was then removed and replaced by a PBS solution. For basal conditions, the plate was kept in the dark during the irradiation time. For irradiated conditions, the cells were irradiated with UVB—275 mJ/cm$^2$ (+UVA—2 J/cm$^2$) using a SOL500 Sun Simulator equipped with an H2 filter (Dr. Hönle, AG). After irradiation time, the treatments were renewed, and the cells were incubated for 24 hours. All experimental conditions were performed in n=3. At the end of incubation, the cells were washed in phosphate buffered saline (PBS) solution and immediately frozen at −80° C.

Differential Expression Analysis

The expression of markers was analyzed using RT-qPCR method on total RNA extracted from the cell monolayers of each experimental condition (before RNA extraction, the replicates of the same experimental condition were pooled). The analysis of transcripts was performed in n=2 using a PCR array dedicated to research and adapted to 'screening' format and targeting 8 genes selected for their role in Nrf2 pathway.

RNA Extraction and Reverse Transcription

Total RNA was extracted from each sample using TriPure Isolation Reagent® according to the supplier's instructions. The amount and quality of RNA were evaluated using capillary electrophoresis (Bioanalyzer 2100, Agilent technologies). The complementary DNA (cDNA) was synthetized by reverse transcription of total RNA in presence of oligo(dT) and «Transcriptor Reverse Transcriptase» (Roche Molecular System Inc.). The cDNA quantities were then adjusted before PCR.

Quantitative PCR

The PCR (Polymerase Chain Reaction) were performed using the «LightCycler®» system (Roche Molecular System Inc.) according to the supplier's instructions. The reaction mix (10 µl final) was prepared as follows:

2.5 µl of cDNA,
primers (forward and reverse),
reagent mix (Roche) containing taq DNA polymerase, SYBR Green I and MgCl2.

The incorporation of fluorescence in amplified DNA was continuously measured during the PCR cycles. This resulted in a "fluorescence intensity" versus "PCR cycle" plot allowing the evaluation of a relative expression (RE) value for each marker. The value selected for RE calculations is the "output point" (Ct) of the fluorescence curve. For a considered marker, the highest is the cycle number; the lowest is the mRNA quantity. The RE value was calculated with the formula: $(\frac{1}{2}^{number\ of\ cycles}) \times 10^6$. The PCR array used in the present study included 1 reference gene (RPS28).

RESULTS AND CONCLUSION

Preliminary Cytotoxicity Assay

The results of the preliminary cytotoxic assay are presented in Table 1.

TABLE 1

Effect of compound L-Ergothioneine and Resveratrol on the viability of keratinocytes after 24 hours of incubation

| | | L-Ergothioneine Unit: µM Stock solution prepared at 43611 µM in Ulltrapure water | | | | | | | | |
|---|---|---|---|---|---|---|---|---|---|---|
| | Control | | 2.2 | 6.7 | 20 | 60 | 180 | 540 | 1620 | 4860 |
| Viability (%) | 102 | 95 | 97 | 97 | 102 | 97 | 95 | 98 | 91 | 79 |
| | 99 | 100 | 97 | 98 | 99 | 100 | 99 | 100 | 89 | 82 |
| | 102 | 102 | 105 | 101 | 97 | 99 | 99 | 0 | 95 | 89 |

TABLE 1-continued

Effect of compound L-Ergothioneine and Resveratrol on the viability of keratinocytes after 24 hours of incubation

| | | | | | | | | | |
|---|---|---|---|---|---|---|---|---|---|
| Mean (%) | 100 | 100 | 99 | 99 | 99 | 97 | 66 | 92 | 83 |
| sem (%) | 1 | 3 | 1 | 1 | 1 | 1 | 33 | 2 | 3 |
| Morphologicalobservations | + | + | + | + | + | + | + | + | + |

| | Control | Resveratrol Unit: µM Stock solution prepared at 50 mM in DMSO | | | | | | | |
|---|---|---|---|---|---|---|---|---|---|
| | | 0.247 | 0.741 | 2.2 | 6.7 | 20 | 60 | 180 | 540 |
| Viability (%) | 103  96 | 101 | 102 | 109 | 109 | 97 | 65 | 32 | 8 |
| | 109  99 | 98 | 100 | 105 | 108 | 93 | 67 | 32 | 8 |
| | 101  91 | 99 | 99 | 105 | 101 | 88 | 64 | 29 | 8 |
| Mean (%) | 100 | 99 | 101 | 106 | 106 | 93 | 65 | 31 | 8 |
| sem (%) | 2 | 1 | 1 | 1 | 3 | 3 | 1 | 1 | 0 |
| Morphologicalobservations | + | + | + | + | + | + | * | * | –, * |

+: normal population; +/–: growth reduction; –: toxicity; 0: cell mortality g: grains of compound; op: opacity of the compound; *: morphological modification; ag: agglutinated cells Effect on Gene Expression Gene expression results are presented in Tables 2-4.

TABLE 2

Validation of the effect of UVB (+UVA) irradiation on gene expression profile of keratinocytes

| mQPA-8-Nrf2 | Genes Abbreviation | Control- Cycles | Irradiated condition UVB - 275 mJ/cm$^2$ (+UVA -2 J/cm$^2$) | |
|---|---|---|---|---|
| | | | Cycles | % Control RPS28 |
| Housekeeping | RPS28 | 20.56 | 20.35 | 100 |
| | | 20.56 | 20.29 | |
| Oxidative and cellular stress response | NQO1 | 32.77 | 32.10 | 101 |
| | | 32.09 | 32.18 | |
| | HMOX1 | 28.44 | 26.10 | 404 |
| | | 28.31 | 26.14 | |

TABLE 2-continued

Validation of the effect of UVB (+UVA) irradiation on gene expression profile of keratinocytes

| mQPA-8-Nrf2 | Genes Abbreviation | Control- Cycles | Irradiated condition UVB - 275 mJ/cm$^2$ (+UVA -2 J/cm$^2$) | |
|---|---|---|---|---|
| | | | Cycles | % Control RPS28 |
| | MT1G | 26.16 | 27.53 | 34 |
| | | 26.16 | 27.43 | |
| | TXN | 19.35 | 19.61 | 79 |
| | | 19.38 | 19.34 | |
| | TXNRD1 | 23.34 | 24.21 | 50 |
| | | 23.35 | 24.03 | |
| | GCLC | 26.15 | 26.95 | 43 |
| | | 25.79 | 26.89 | |
| | GCLM | 24.82 | 26.01 | 35 |
| | | 24.72 | 26.08 | |

TABLE 3

Effects of reference Resveratrol and compound L-Ergothioneine on gene expression profile of keratinocytes under basal conditions

| | | Control | Resveratrol 20 µM | | L-Ergothioneine 0.5 µM | | 3 µM | | 30 µM | |
|---|---|---|---|---|---|---|---|---|---|---|
| | | Cycles | Cycles | % Control RPS28 | Cycles | % Control RPS28 | Cycles | % Control RPS28 | Cycles | % Control RPS28 |
| Housekeeping | | 20.56 | 20.69 | 100 | 20.48 | 100 | 20.33 | 100 | 20.53 | 100 |
| | | 20.56 | 20.91 | | 20.49 | | 20.47 | | 20.36 | |
| Oxidative and cellular stress response | NQO1 | 32.77 | 28.76 | 1468 | 31.95 | 127 | 31.86 | 131 | 31.55 | 155 |
| | | 32.09 | 28.74 | | 32.00 | | 31.81 | | 31.73 | |
| | HMOX1 | 28.44 | 26.35 | 451 | 28.50 | 86 | 28.54 | 91 | 28.24 | 98 |
| | | 28.31 | 26.53 | | 28.54 | | 28.19 | | 28.33 | |
| | MT1G | 26.16 | 26.77 | 79 | 25.85 | 113 | 26.08 | 99 | 25.86 | 115 |
| | | 26.16 | 26.71 | | 25.98 | | 25.95 | | 25.82 | |
| | TXN | 19.35 | 17.80 | 345 | 19.39 | 87 | 19.34 | 83 | 19.27 | 98 |
| | | 19.38 | 17.83 | | 19.61 | | 19.60 | | 19.29 | |
| | TXNRD1 | 23.34 | 21.35 | 492 | 23.76 | 75 | 23.65 | 72 | 23.52 | 82 |
| | | 23.35 | 21.22 | | 23.63 | | 23.67 | | 23.52 | |
| | GCLC | 26.15 | 23.73 | 554 | 25.81 | 111 | 25.50 | 118 | 25.44 | 140 |
| | | 25.79 | 23.72 | | 25.66 | | 25.61 | | 25.28 | |
| | GCLM | 24.82 | 22.14 | 736 | 24.77 | 95 | 24.66 | 97 | 24.65 | 98 |
| | | 24.72 | 22.11 | | 24.78 | | 24.64 | | 24.70 | |

TABLE 4

Effects of compound L-Ergothioneine on gene expression profile of keratinocytes under UV-irradiated conditions
Irradiated conditions: UVB - 275 mJ/cm$^2$ (+UVA - 2 J/cm$^2$)

| mQPA-8-Nrf2 | | Control Cycles | L-Ergothioneine | | | | | |
|---|---|---|---|---|---|---|---|---|
| | | | 0.5 µM | | 3 µM | | 30 µM | |
| | | | Cycles | % Control RPS28 | Cycles | % Control RPS28 | Cycles | % Control RPS28 |
| Housekeeping | | 20.35 | 20.37 | 100 | 20.26 | 100 | 20.52 | 100 |
| | | 20.29 | 20.13 | | 20.33 | | 20.65 | |
| Oxidative and cellular stress response | NQO1 | 32.10 | 31.98 | 118 | 31.63 | 136 | 31.24 | 207 |
| | | 32.18 | 31.69 | | 31.72 | | 31.47 | |
| | HMOX1 | 26.10 | 25.94 | 104 | 26.05 | 109 | 25.92 | 141 |
| | | 26.14 | 26.05 | | 25.90 | | 25.85 | |
| | MT1G | 27.53 | 27.67 | 81 | 27.52 | 94 | 27.72 | 102 |
| | | 27.43 | 27.74 | | 27.57 | | 27.72 | |
| | TXN | 19.61 | 19.56 | 89 | 19.45 | 99 | 19.65 | 101 |
| | | 19.34 | 19.58 | | 19.48 | | 19.78 | |
| | TXNRD1 | 24.21 | 24.14 | 99 | 24.15 | 97 | 24.07 | 120 |
| | | 24.03 | 23.99 | | 24.13 | | 24.16 | |
| | GCLC | 26.95 | 26.75 | 106 | 26.58 | 126 | 26.30 | 181 |
| | | 26.89 | 26.78 | | 26.55 | | 26.36 | |
| | GCLM | 26.01 | 26.49 | 76 | 26.23 | 86 | 26.47 | 86 |
| | | 26.08 | 26.24 | | 26.24 | | 26.57 | |

At the end of the culture and after a morphological observation of cells, it turned out that the viability of NHEK treated with resveratrol under irradiated condition was strongly impacted. The treatment of the NHEK with the reference compound, resveratrol, tested at 20 resulted in the stimulation of the expression of all genes (except MT1G) involved in oxidative and cellular stress response: NQO1, HMOX1, TXN, TXNRD1, GCLC and GCLM. These results were expected and validated the assay.

Under the experimental conditions of the assay, compound L-Ergothioneine, tested at 0.5, 3 and 30 µM did not induce major modulations on the gene expression profile of basal keratinocytes. At the highest tested concentration (30 compound L-Ergothioneine only slightly increased (140% of the control) the expression of GCLC (Glutamate-cysteine ligase, catalytic subunit). At the lowest tested concentrations, no effect was observed.

The UVB (+UVA) irradiation at 275 mJ/cm$^2$ (+2 J/cm$^2$) resulted in a clear modulation of the gene expression profile of normal human epidermal keratinocytes (NHEK). More specifically, the irradiation mainly induced an up-regulation of a marker of the early oxidative stress response (HMOX1 involved in the first response to oxidative stress), and a down-regulation of the expression of genes involved in oxidative and cellular stress response (MT1G, TXNRD1, GCLC and GCLM). Under the experimental conditions of the assay, compound L-Ergothioneine, tested at 0.5, 3 and 30 did not induce major modulations on the gene expression profile of irradiated keratinocytes. At the highest tested concentration (30 compound L-Ergothioneine only slightly increased the expression of GCLC (181% of the stimulated control) and in a lesser extent HMOX1 (141% of the stimulated control). At the lowest tested concentrations, no effect was observed.

Example 2. Effects of Oral L-ergothioneine (25 mg/Day) on Plasma Glutathione in Healthy Humans Protocol Synopsis
Title of Study:
Effects of Oral L-Ergothioneine on Plasma Glutathione
Study Period:
4 weeks
Test Product:
L-Ergothionine 25 mg/capsule (consumed once daily for 30 days with other supplements or at main meal)
Comparator Products:
Glutathione (1400 mg) adminstered IV once per week and S-acetyl-glutathione (200 mg;) adminstered orally once daily
Objectives:
1. To demonstrate the tolerability of oral administration of 25 mg ergothioneine
2. To demonstrate the ability of oral administration of 25 mg ergothioneine to increase plasma GSH
Design:
Following enrollment, subjects will be randomly assigned to either receive one IV of glutathione, 1400 mg, once weekly for four weeks, 5-acetyl glutathione, 200 mg a day for four weeks, or L-ergothioneine, once daily for four weeks. A Baseline will be established looking at Total and Percent Reduced Glutathione. These same values will be measured at the end of the four weeks. Subjects will be contacted once a week while in the study for an assessment of compliance with intervention.
Study Population:
Male and female subjects 25-75 years of age
Number of Subjects:
5, assigned as follows: 1 subject will receive the GSH administered once weekly for 4 weeks; 1 subject will receive S-acetyl-glutathione once daily for 4 weeks; 3 subjects will receive L-ergothioneine once daily for 4 weeks Inclusion Criteria:
1. Individuals must be between 25-70 years of age with no known medical conditions that, in the investigator's opinion, may interfere with study participation.
2. Subjects must present with mild to moderate signs oxidative stress or inflammation.
3. Willingness to cooperate and participate by following Study requirements.
4. Individuals must sign informed consent, photo release consent and confidentiality agreement.

Exclusion Criteria:
1. Any Individuals that are being treated for cancer or have cancer.
2. Individuals currently taking certain medications or any dietary supplements, which in the opinion of the investigator might interfere with the study. This would include but not be limited to routine high dosage use of anti-inflammatory drugs (aspirin, ibuprofen, corticosteroids) immunosuppressive drugs or antihistamine medications), and insulin, antihypertensive drugs, and especially antioxidants.
3. Individuals with uncontrolled metabolic diseases such as diabetes (Type I and II), hypertension, hyperthyroidism or hypothyroidism, severe chronic asthma, immunological disorders such as HIV positive, AIDS and systemic lupus erythematosus or mastectomy for cancer involving removal of lymph nodes.
4. Women known to be pregnant, nursing or planning to become pregnant.
5. Individuals participating in other clinical studies evaluating antioxidants or anti-inflammatory interventions.

RESULTS AND CONCLUSIONS

Study results are depicted in the FIGURE.

Subjects received 25 mg L-ergothioneine or 200 mg S-acetyl-glutathione (SAG; comparator intervention) for 1 month. The one subject who was received GSH iv contracted Covid-19 during the study, and did not complete the study. No data are provided for this single subject. No adverse events were reported, and compliance L-ergothioneine and SAG was excellent, based on the counting of test materials at the end of the study.

The 3 study subjects that received L-ergothioneine 25 mg daily po had different levels of total GSH at baseline, ranging from 353 µM to 584 µM. The single subject taking the comparator, SAG, had a baseline level of total GSH of 727 µM. The three study subjects that received L-ergothioneine 25 mg daily po all exhibited increased levels of total GSH at Day 30, ranging from 502 µM to 867 µM. The single study subject that received the comparator intervention, SAG, showed a reduction in total GSH of 547 µM. The % change from baseline through Day 30 of three study subjects that received L-ergothioneine ranged from 13% (IB) to 146% (ST). The % change from baseline of the study subject that received SAG was −25%.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating a glutathione deficiency in a human patient in need thereof comprising administering to the patient a therapeutically effective amount from 15 to 50 mg/day of L-ergothioneine or a pharmaceutically acceptable salt thereof, wherein the patient is suffering from GSH RBC levels ≤1,200 µmol/L.

2. A method of treating a glutathione synthetase deficiency causing hemolytic anemia in a human patient in need thereof comprising administering to the patient a therapeutically effective amount from 15 to 50 mg/day of L-ergothioneine or a pharmaceutically acceptable salt thereof, wherein the patient is suffering from GSH RBC levels ≤1,200 µmol/L.

3. The method of claim 2, wherein the patient has glutathione synthetase deficiency causing hemolytic anemia (OMIM 231900).

4. A method of treating a generalized glutathione synthetase deficiency with 5-oxoprolinuria in a human patient in need thereof comprising administering to the patient a therapeutically effective amount from 15 to 50 mg/day of L-ergothioneine or a pharmaceutically acceptable salt thereof, wherein the patient is suffering from GSH RBC levels ≤1,200 µmol/L.

5. The method of claim 4, wherein the patient is suffering from glutathione synthetase deficiency with 5-oxoprolinuria (OMIM 266130).

6. The method of claim 1, wherein the glutathione deficiency is characterized by a reduction in Nrf2 regulated genetic activity.

7. The method of claim 2, wherein the glutathione deficiency is characterized by a reduction in Nrf2 regulated genetic activity.

8. The method of claim 7, wherein the patient has glutathione synthetase deficiency causing hemolytic anemia (OMIM 231900).

9. The method of claim 4, wherein the glutathione deficiency is characterized by a reduction in Nrf2 regulated genetic activity.

10. The method of claim 9, wherein the patient is suffering from glutathione synthetase deficiency with 5-oxoprolinuria (OMIM 266130).

11. The method of claim 1, wherein the therapeutically effective amount comprises about 20 or 25 mg/day of L-ergothioneine or a pharmaceutically acceptable salt thereof.

12. The method of claim 1, wherein the L-ergothioneine is administered as an oral dosage form comprising from 15 to 50 mg of L-ergothioneine.

13. The method of claim 1, wherein the L-ergothioneine is administered as an oral dosage form comprising about 20 mg or 25 mg of L-ergothioneine.

14. The method of claim 1, wherein the L-ergothioneine comprises 0% D-ergothioneine, 0% nucleic acids, 0% amino acids, and less than 2% total impurities.

15. The method of claim 1, wherein the L-ergothioneine is administered in the form of a tablet, capsule, powder sachet, or liquid.

16. The method of claim 1, wherein the patient is suffering from one or a combination of plasma levels of:
   a) reduced glutathione (GSH)≤3.8, 3.5, or 3.2 µmol/L;
   b) oxidized glutathione (GSS)≤0.160, 0.130, or 0.100 µmol/L; and/or
   c) total glutathione (GSH+GSS)≤3.8, 3.5, or 3.2 µmol/L.

17. The method of claim 1, wherein the patient is suffering from one or a combination of:
   a) lack of energy;
   b) joint and muscle aches and pains;
   c) foggy brain;
   d) low immunity; and/or
   e) poor sleep.

18. The method of claim 1, wherein the patient is suffering from one or a combination of:
   a) anemia;
   b) metabolic acidosis;
   c) frequent infections;
   d) seizures, Alzheimer's disease, or Parkinson's disease;
   e) ataxia;
   f) liver disease; and/or
   g) heart attack or stroke.

\* \* \* \* \*